United States Patent
Holler et al.

(10) Patent No.: US 8,611,491 B2
(45) Date of Patent: Dec. 17, 2013

(54) COMPRESSION PLATE FOR A MAMMOGRAPHY UNIT AND A MAMMOGRAPHY UNIT

(75) Inventors: Wolfgang Holler, Erlangen (DE); Martin Ramsauer, Pyrbaum (DE)

(73) Assignee: Siemens Aktiengesellschaft, München (DE)

( * ) Notice: Subject to any disclaimer, the term of this patent is extended or adjusted under 35 U.S.C. 154(b) by 674 days.

(21) Appl. No.: 11/990,808

(22) PCT Filed: Jul. 21, 2006

(86) PCT No.: PCT/EP2006/064494
§ 371 (c)(1),
(2), (4) Date: Jun. 30, 2009

(87) PCT Pub. No.: WO2007/023050
PCT Pub. Date: Mar. 1, 2007

(65) Prior Publication Data
US 2009/0299218 A1    Dec. 3, 2009

(30) Foreign Application Priority Data
Aug. 22, 2005   (DE) .......................... 10 2005 039 658

(51) Int. Cl.
*A61B 6/04*    (2006.01)
(52) U.S. Cl.
USPC ............................................ 378/37; 378/206
(58) Field of Classification Search
USPC ................ 600/567, 426; 378/37, 206
See application file for complete search history.

(56) References Cited

U.S. PATENT DOCUMENTS

| 5,170,419 | A | 12/1992 | Johansson et al. |
| 5,320,111 | A | 6/1994 | Livingston |
| 5,660,185 | A * | 8/1997 | Shmulewitz et al. ......... 600/562 |
| 6,102,866 | A * | 8/2000 | Nields et al. .................. 600/461 |
| 6,423,076 | B1 * | 7/2002 | Cardwell et al. ............... 606/130 |
| 7,238,177 | B2 * | 7/2007 | Somani et al. .................... 606/5 |
| 2003/0210548 | A1 | 11/2003 | Lin |
| 2004/0116914 | A1 * | 6/2004 | Dowlatshahi ................... 606/10 |

FOREIGN PATENT DOCUMENTS

| EP | 0 002 244 A1 | 6/1979 |
| JP | 08080295 A | 3/1996 |
| WO | WO 93/15683 | 8/1993 |

OTHER PUBLICATIONS

International Search Report dated Dec. 18, 2006, and translation of the PCT Written Opinion for International Application No. PCT/EP2006/064494.
"Laser Positioner," Copyright©2007 Livingston Products Inc., obtained at Internet address http://www.livingstonproducts.com/mammo/LaserPos.html.

\* cited by examiner

*Primary Examiner* — Max Hindenburg
*Assistant Examiner* — Renee Danega
(74) *Attorney, Agent, or Firm* — Lempia Summerfield Katz LLC

(57) ABSTRACT

A laser device for projecting a position mark in the field of vision onto an object to be examined using a mammography unit is described, where the laser device can be adjusted in position together with a vertically adjustable compression plate of the mammography unit. The laser device may be arranged on the compression plate or on the compression plate support thereof. In the latter configuration, the laser device may remain attached to the mammography unit. The apparatus has application to biopsies.

17 Claims, 4 Drawing Sheets

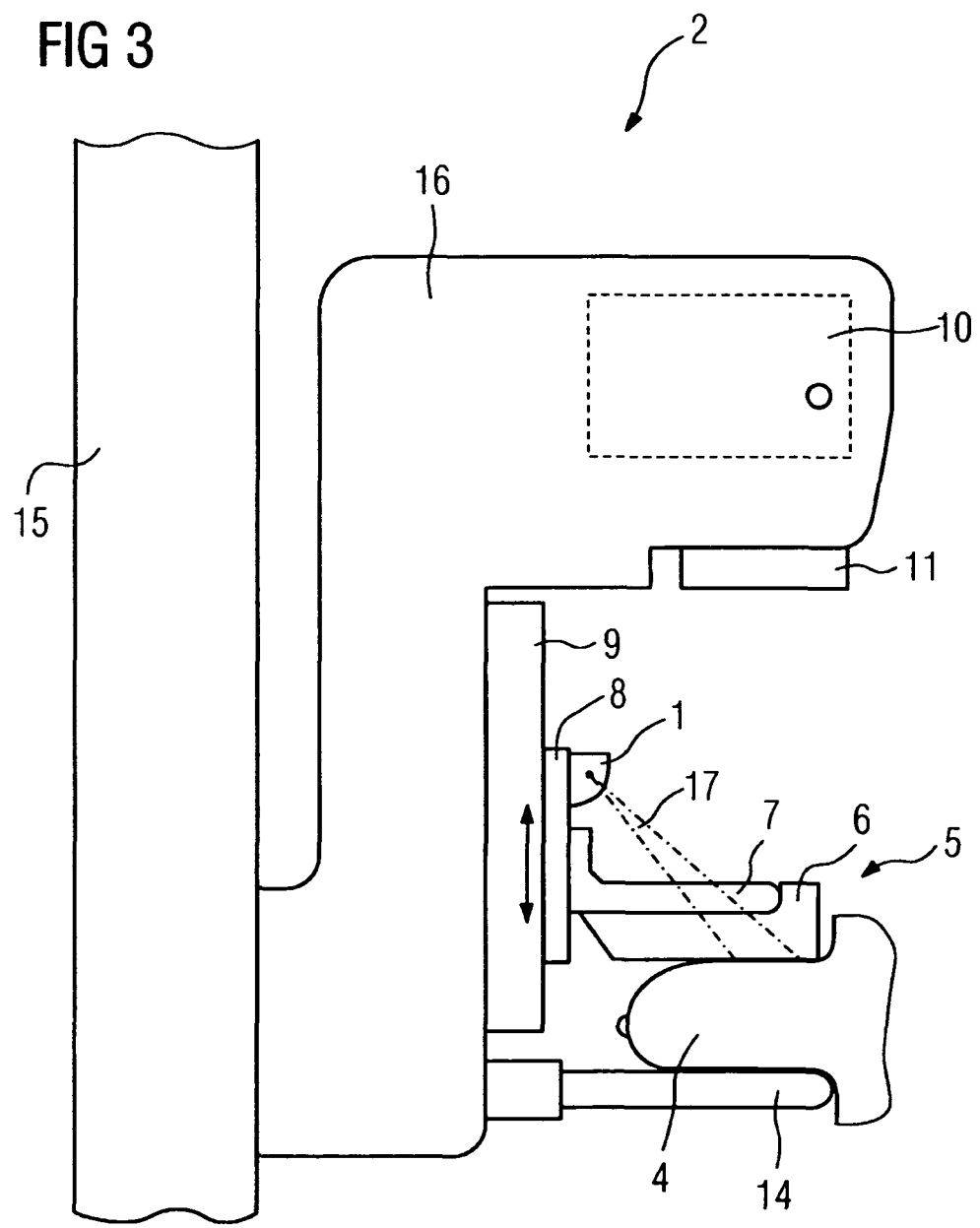

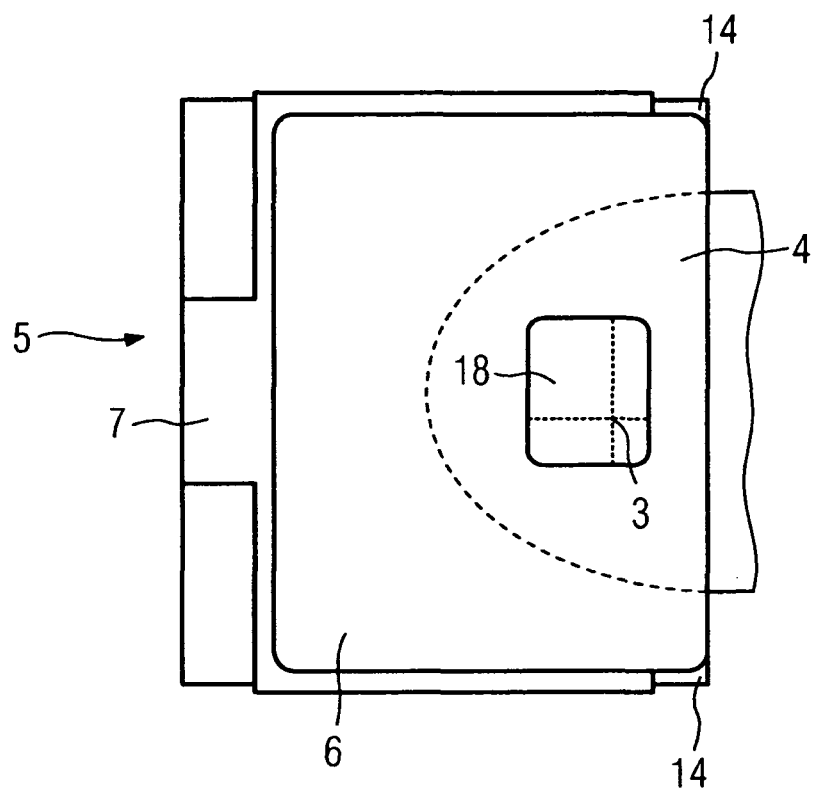

COMPRESSION PLATE FOR A MAMMOGRAPHY UNIT AND A MAMMOGRAPHY UNIT

TECHNICAL FIELD

The present application invention relates to a laser marking device for a mammography device.

BACKGROUND

A mammography unit is an X-ray system for examining a breast of a patient. Before beginning to take an X-ray, the object being examined is placed on an object table, belonging to a mammography unit and having an X-ray receiver, and is compressed by a compression plate. Typically, the compression plate is disposed on an adjustable-height compression plate mounting of the mammography unit by means of a releasable mounting mechanism, which makes it possible for the particular compression plate to be exchanged for a compression plate intended for the particular examination method or the particular object being examined. A mammography unit of this kind is disclosed for instance in U.S. Pat. No. 5,170,419 A.

For performing a biopsy of the particular object being examined, special compression plates are provided, with an opening that allows access to the particular region to be examined of the object being examined. For position marking a puncture point for the biopsy, a shadow cross device is known that can be disposed in front of an X-radiation diaphragm of the mammography unit and in a light projection of a light visor makes a particular position detectable by means of a cross-shaped shadow. The particular position marked is adjustable manually relative to a scale located beside the opening on the compression plate. This kind of shadow cross device can be procured as accessory equipment from Siemens AG (Munich, Germany), as an example.

For position marking, instead of the shadow cross device, the laser device known as "Laser Positioner II" made by Livingston Products Inc (Buffalo Grove, Ill.). can also be disposed on the X-radiation diaphragm; this laser device marks the particular position by projecting a position marking in the shape of a cross. Since the laser emitter of the laser device is offset from the X-radiation, a parallax error can occur, depending on the spacing between the laser device and the object being examined; this error is corrected by an automatic correction of the projection angle of the laser emitter.

For X-ray images that are intended to perform a biopsy, the laser device is positioned at a distance from the X-radiation diaphragm, since it limits the X-radiation field and hinders the view of the object being examined and makes access to the object being examined more difficult. The power supply is provided via a battery located in the laser device; in this way, the need for making a power connection with the mammography unit in addition to attaching the laser device is avoided.

FIG. 1 shows a mammography unit 2 in accordance with the related art; including a support member 15, a mounting arm 16 located on the support member 15; an X-ray emitter 10 for generating X-radiation 13, disposed on the upper end of the mounting arm 16; an X-radiation diaphragm 11 for delimiting the X-radiation 13 onto an intended X-radiation field, an adjustable-height compression plate 5; and, an X-ray receiver 14 located on the lower end of the mounting arm 16. In FIG. 1, the contour of the maximum radiation field of the X-radiation 13 is shown. The X-radiation 13 penetrates a particular object being examined 4 before striking the X-ray receiver 14 that generates an X-ray image of the object being examined 4.

The object being examined 4 is compressed by the compression plate 5, which includes both a mounting frame 7 and a transparent compression member 6. The compression plate is releasably connected to a compression plate mounting 8 that is located on a guide 9 of the mammography unit 2, and is adjustable in height.

A shadow cross device 12, with which a position marking in the shape of a shadow cross can be projected onto the object being examined 4, is located on the X-radiation diaphragm 1. As a result, for instance in a biopsy, a particular intended puncture point on the object being examined 4 can be marked. The shadow cross devices 12 like all the other devices that can be disposed on the diaphragm 11 of the mammography unit 2 for projecting a position marking, restrict the X-radiation field to only a fraction of the maximum possible X-radiation field. To make a full-field image of the object being examined 4 with the mammography unit 2, the shadow cross device 12 has to be removed from the diaphragm 11.

SUMMARY AND DESCRIPTION

A laser device for projecting a position marking in the field of view onto the particular object being examined using a mammography unit is provided. A compression plate, which can be joined adjustably with a mammography unit, has a laser device. In one embodiment, it is possible for the laser device to remain on the mammography unit.

Because the laser device is jointly displaceable with the adjustable-height compression plate, the position of the laser device relative to the compression plate mounting remains unchanged and thus, despite a possible lateral projection, it is possible to dispense with a new correction of the projection angle, in order to avoid a parallax error. An exact position marking is thus reliably assured.

The projection is done in such a way that the position marking in the field of view of the particular object being examined is recognizable to a person operating the mammography unit. The recognizability in the field of view is assured by providing that the position marking can be projected onto the object being examined itself. The projection is done for instance through a transparent part of the compression plate.

Alternatively, a projection of the position marking onto the compression plate is possible; as a result, in the case of a lateral projection, the index of refraction of the transparent part of the compression plate need not be taken into account. For better recognizability of the position marking, the compression plate can be excited to fluoresce under the influence of the laser light projected by the laser device; as a result, the position marking is especially clearly recognizable, even if ultraviolet laser light is used for the projection.

The position marking may take various forms. By means of a position marking in the shape of a cross, the particular marked position can be projected with particular clarity. The position marking in the shape of the cross may be generated by two line lasers of the laser device. The projection of the cross may be generated by projecting two lines that are each projected by one of the two line lasers. Alternatively, the position marking in the shape of the cross may be generated by a point laser and a refractive optical element; as a result, projecting the cross can be done with only a single laser. The refractive optical element generates a cross-shaped projection from an initially point-shaped laser beam. The projection of the position marking may be accomplished by means of a position marking in the form of a point. In addition, further shapes for the position marking are conceivable, such as a circle. For a position marking which, similarly to the point marking, does not make any reference possible to a scale located laterally of a particular position to be marked, a scale is provided on an adjusting device provided for adjusting the particular marking position. This adjusting device may, for instance, be two rotary knobs located on the laser device that make it possible to adjust the position of the projection in directions perpendicular to one another.

Because the particular position marked with the position marking is adjustable, in a manual or automatic manner, flexible adaptation of the position to the particular examination or the particular biopsy is possible. As the laser device can be disposed on the compression plate, the compression plate can be replaced together with the laser device. This is useful for a compression plate intended for performing a biopsy of the object being examined. Alternatively, the laser device may be disposed on a compression plate mounting of the mammography unit. The laser device may then be used with different compression plates that can each be secured to the compression plate mounting.

The result may also be attained by a compression plate having one of the aforementioned laser devices. Where the compression plate is capable of being disposed height-adjustably on a mammography unit; it may be possible to use the compression plate along with the laser device as accessory equipment on the mammography unit.

In another aspect, a compression plate mounting having one of the aforementioned laser devices allows retrofitting the laser device by replacing an existing compression plate mounting on the mammography unit. Since the laser device is disposed on the compression plate mounting, the field of view onto the object being examined is unrestricted by the laser device or the mounting thereof, and thus the laser device may remain on the mammography unit throughout the procedure, and may be subsequently left in place. Moreover, when the laser device is disposed permanently on the mammography unit, it is possible to supply power to the laser device via a power connection to the mammography unit. Securing and removing an additional device for position marking, such as the shadow cross device, is thus avoided.

BRIEF DESCRIPTION OF THE DRAWINGS

FIG. 3 shows a side view of a mammography unit as in FIG. 2, having a laser device located on the compression plate mounting; and FIG. 4 shows a plan view of an object being examined being compressed by the compression plate, and a projected laser-light cross.

DESCRIPTION

Exemplary embodiments may be better understood with reference to the drawings, but these embodiments are not intended to be of a limiting nature. Like numbered elements in the same or different drawings perform equivalent functions.

Figure 1:
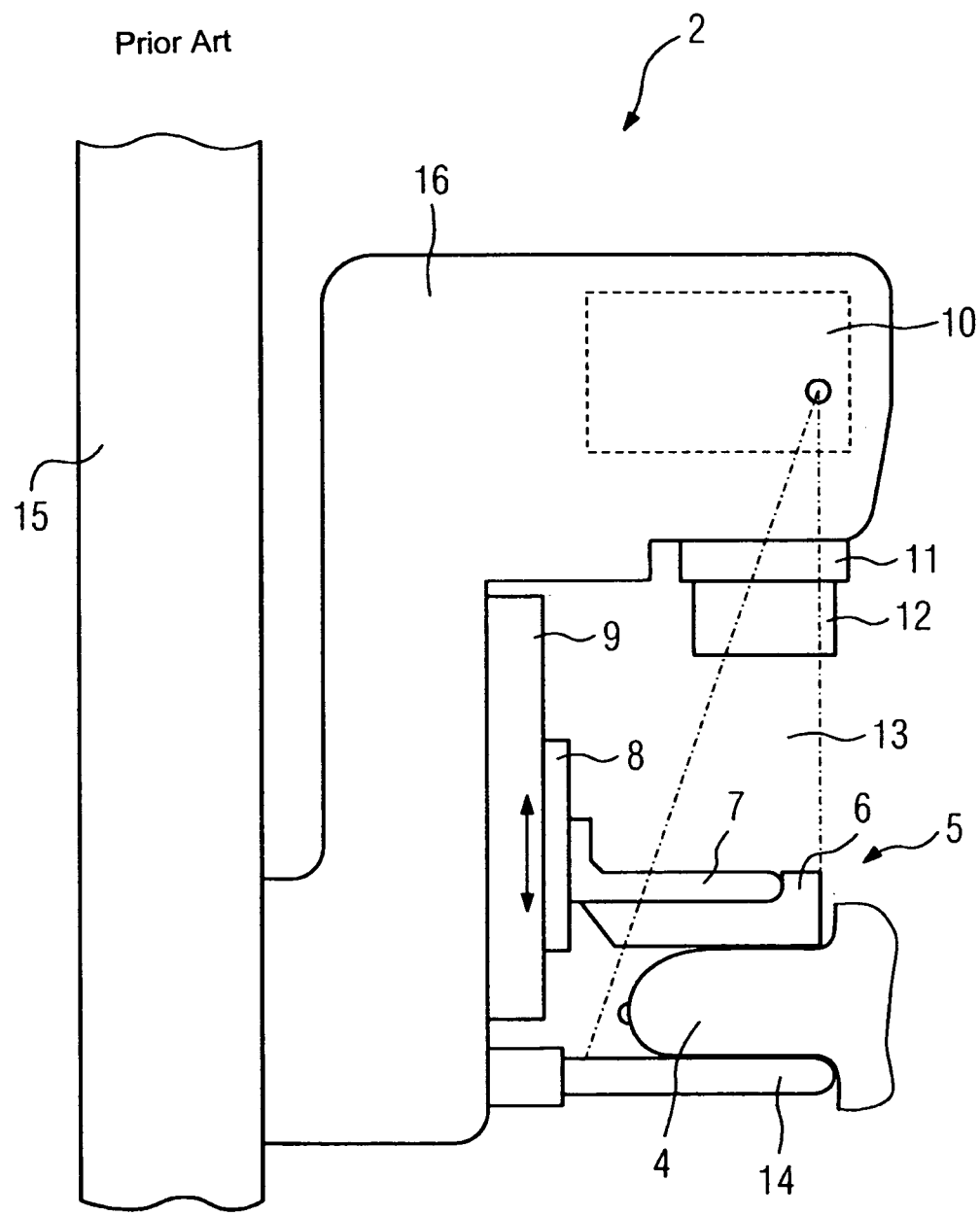
FIG. 1 shows a side view of a mammography unit in accordance with the related art, with a shadow cross device located on a diaphragm for projecting a position marking in the shape of a shadow cross.
Figure 2:
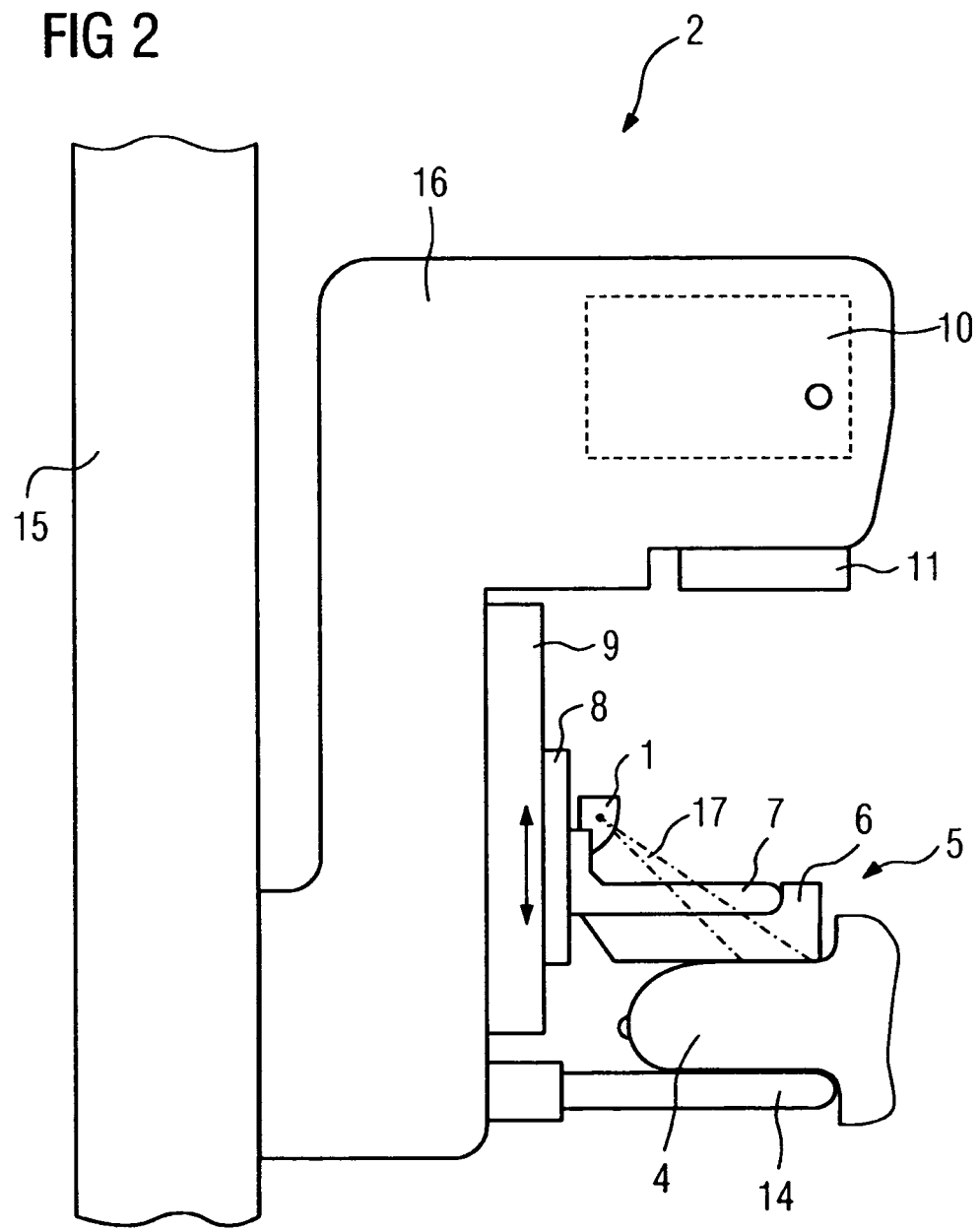
FIG. 2 shows a side view of a mammography unit of one embodiment having a laser device located on a compression plate.

FIG. 2 shows a side view of a mammography unit 2, with a laser device 1 located on the compression plate 5, instead of the shadow cross device 12 located on the X-radiation diaphragm 11 as in FIG. 1. The laser device 1 may emit a laser beam 17 which is aimed at the object being examined 4 and projects a position marking in the shape of a laser-light cross onto the object being examined 4. Due to the stationary position of the laser device 1 relative to the compression plate 5, which rests directly on the object being examined 4, the projection of the laser beam 17 may be made repeatedly in the same coordinates with respect to the compression plate when the height of the compression plate 5 is varied. The compression plate 5 may be replaced or removed together with the laser device 1 located on it. An enlarged view of the compression plate 5, in a plan view, is shown in FIG. 4.

In another aspect, FIG. 3 shows a side view of the mammography unit 2 in where the laser device 1 is located on the adjustable-height compression plate mounting 8. In this disposition of the laser device 1 in the part of the working area nearer the support member 15, between the X-radiation diaphragm 11 and the X-ray receiver 14, the laser device 1 neither limits access to the object being examined 4 nor limits the usable X-radiation field, so that the laser device 1 may remain attached to the mammography unit 2, without reducing the functionality of the mammography unit 2. In this permanent disposition of the laser device 1, the power supply can be provided by way of a power connection with the mammography unit 2. Moreover, the same laser device 1 maybe used for projecting the position marking, even if different compression plates 5 are used.

FIG. 4 shows a plan view of the object being examined 4 that has been compressed by the compression plate 5. For a compression plate 5 that may be designed for biopsy, there is an opening 18 in the transparent compression member 6, and this opening may permit access to the object being examined 4. Inside the opening 18, the position marking 3 may be projected in the shape of a laser-light cross onto the object being examined 4 by the laser device 1. The laser-light cross may comprise two lines perpendicular to one another, each projected by one line laser of the laser device 1. Additional distance measurement scales (not shown), which make it easier to adjust the particular desired position, may be disposed on the transparent compression member 6, on the sides of the opening 18.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. An apparatus for use on a mammography unit, the apparatus comprising:
   a compression plate adjustably attached to a support of the mammography unit, such that the compression plate is operable to compress an object to be examined against a support member, the support member supporting the object to be examined; and
   a laser on the compression plate and adapted to project laser light so as to form a position mark on the object to be examined.

2. The apparatus of claim 1, wherein the position mark is projected onto the object to be examined.

3. The apparatus of claim 1, wherein the position mark is projected onto the compression plate, and the compression plate is excited to fluoresce by the laser light projected by the laser.

4. The apparatus of claim 1, wherein the position mark is in the shape of a cross.

5. The apparatus of claim 4, wherein the laser device has two line lasers for projecting the cross position mark.

6. The apparatus of claim 4, wherein the laser device has a point laser and a refractive optical element for projecting the cross.

7. The apparatus of claim 1, wherein the position mark is in the form of a point.

8. The apparatus of claim 1, wherein the position mark is manually adjustable.

9. The apparatus of claim 1, wherein the laser device is disposed on the compression plate, the compression plate being adapted to accommodate a biopsy procedure.

10. The apparatus of claim 1, wherein the laser device is disposed on a compression plate mounting of the mammography unit.

11. The apparatus of claim 3, wherein the position mark is in the shape of a cross.

12. The apparatus of claim 3, wherein the position mark is in the form of a point.

13. A mammography unit comprising:
an X-ray source and an X-ray detector; and
a compression plate adjustably attached to a support of the X-ray source and the X-ray detector, and having a laser adapted to project laser light for marking a position in the radiological field of view of an object, the laser being on the compression plate,
wherein the compression plate is operable to compress an object to be examined against the X-ray detector.

14. A method of performing a biopsy, the method comprising:
providing a mammography unit having a compression plate, the compression plate releasably attachable to a compression plate mounting;
compressing an object to be examined against a support member with the compression plate; and
identifying a puncture point for a biopsy by marking the position of the puncture point with light from a laser on the compression plate.

15. A mammography unit comprising:
an X-ray source and an X-ray detector;
a compression plate adjustably attached to a support of the X-ray source and the X-ray detector; and
a laser adapted to project laser light for marking a position in a radiological field of view of an object, the laser being on the compression plate such that the laser is stationary relative to the compression plate when the compression plate is moved along the support,
wherein the compression plate is operable to compress an object to be examined against the X-ray detector.

16. The mammography unit of claim 15, further comprising an adjustable height compression plate mounting movably connected to the support of the X-ray source,
wherein the compression plate is releasably connected to the adjustable-height compression plate mounting.

17. The mammography unit of claim 16, wherein the laser is located on the adjustable-height compression plate mounting.

* * * * *